United States Patent
Hagemann et al.

(10) Patent No.: US 12,290,654 B2
(45) Date of Patent: *May 6, 2025

(54) USING ALTERNATING ELECTRIC FIELDS TO INCREASE PERMEABILITY OF THE BLOOD BRAIN BARRIER

(71) Applicant: Novocure GmbH, Root (CH)

(72) Inventors: Carsten Hagemann, Unterpleichfeld (DE); Mario Lohr, Dillenburg (DE); Almuth F. Kessler, Reichenberg (DE); Malgorzata Burek, Wurzburg (DE); Carola Forster, Wurzburg (DE); Catherine Brami, Matan (IL); Hadas Sara Hershkovich, Kiryat Motzkin (IL); Tali Voloshin-Sela, Haifa (IL)

(73) Assignee: Novocure Gmbh, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/741,651

(22) Filed: May 11, 2022

(65) Prior Publication Data
US 2022/0265982 A1    Aug. 25, 2022

Related U.S. Application Data

(63) Continuation of application No. 16/548,514, filed on Aug. 22, 2019, now Pat. No. 11,351,349.

(Continued)

(51) Int. Cl.
*A61N 1/32* (2006.01)
*A61K 9/00* (2006.01)
(Continued)

(52) U.S. Cl.
CPC ....... *A61M 37/0092* (2013.01); *A61K 9/0009* (2013.01); *A61N 1/325* (2013.01);
(Continued)

(58) Field of Classification Search
CPC . A61N 1/327; A61N 1/32; A61M 2037/0007; A61M 2210/0693; A61M 2205/054
See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |
| (Continued) | | |

FOREIGN PATENT DOCUMENTS

| | | |
|---|---|---|
| CN | 1206353 A | 1/1999 |
| CN | 104602759 A | 5/2015 |
| (Continued) | | |

OTHER PUBLICATIONS

Arena et al., "Focal blood-brain-barrier disruption with high-frequency pulsed electric fields," Technology, vol. 2, No. 3, Jul. 2014.

(Continued)

*Primary Examiner* — Emily L Schmidt
(74) *Attorney, Agent, or Firm* — Potomac Law Group, PLLC

(57) ABSTRACT

Certain substances (e.g., large molecules) that ordinarily cannot traverse the blood brain barrier can be introduced into the brain by applying an alternating electric field to the brain for a period of time, wherein the frequency of the alternating electric field is selected so that application of the alternating electric field increases permeability of the blood brain barrier. In some embodiments, the frequency of the alternating electric field is less than 190 kHz (e.g., 100 kHz). Once the permeability of the blood brain barrier has been increased, the substance is able to cross the blood brain barrier.

12 Claims, 9 Drawing Sheets

Related U.S. Application Data

(60) Provisional application No. 62/722,100, filed on Aug. 23, 2018.

(51) Int. Cl.
*A61M 37/00* (2006.01)
*A61N 1/36* (2006.01)
*A61N 1/372* (2006.01)

(52) U.S. Cl.
CPC ......... *A61N 1/327* (2013.01); *A61N 1/36002* (2017.08); *A61N 1/3603* (2017.08); *A61N 1/37217* (2013.01); *A61K 9/0085* (2013.01); *A61M 2037/0007* (2013.01); *A61M 2202/0007* (2013.01); *A61M 2210/0693* (2013.01); *A61M 2250/00* (2013.01)

(56) References Cited

U.S. PATENT DOCUMENTS

| | | |
|---|---|---|
| 7,089,054 B2 | 8/2006 | Palti |
| 7,136,699 B2 | 11/2006 | Palti |
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,758,561 B2 | 7/2010 | Eppstein |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 8,926,606 B2 | 1/2015 | Davalos et al. |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,198,733 B2 | 12/2015 | Neal et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 2002/0193833 A1 | 12/2002 | Dimmer et al. |
| 2003/0158589 A1 | 8/2003 | Katsnelson |
| 2003/0171738 A1 | 9/2003 | Konieczynski et al. |
| 2003/0191506 A1 | 10/2003 | Shloznikov |
| 2004/0010290 A1 | 1/2004 | Schroeppel et al. |
| 2006/0149337 A1 | 7/2006 | John |
| 2006/0276858 A1 | 12/2006 | Palti |
| 2010/0049117 A1 | 2/2010 | Bragagna et al. |
| 2011/0046540 A1 | 2/2011 | Alterman et al. |
| 2011/0079513 A1 | 4/2011 | Stelzle et al. |
| 2012/0310140 A1 | 12/2012 | Kramer et al. |
| 2012/0323214 A1 | 12/2012 | Shantha |
| 2014/0039489 A1 | 2/2014 | Davalos et al. |
| 2014/0154244 A1 | 6/2014 | Desai et al. |
| 2014/0330268 A1 | 11/2014 | Palti et al. |
| 2015/0126964 A1 | 5/2015 | Martel et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0021217 A1 | 1/2018 | Tracey et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0298982 A1 | 10/2019 | Story et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016399 A1 | 1/2020 | Kaynan et al. |
| 2021/0016084 A1 | 1/2021 | Mardor et al. |

FOREIGN PATENT DOCUMENTS

| | | |
|---|---|---|
| CN | 112469352 A | 3/2021 |
| EP | 1502623 A1 | 2/2005 |
| WO | 2016164930 A1 | 10/2016 |
| WO | 2016179712 A1 | 11/2016 |

OTHER PUBLICATIONS

Bonakdar et al., "A microfluidic model of the blood-brain barrier to study permeabilization by pulsed electric fields," RSC Advances, vol. 7, pp. 42811-42818, 2017.

Chang et al., "Tumor treating fields increases membrane permeability in glioblastoma cells," Cell Death Discovery, 4:113, 2018.

Chang et al., "Tumor treating fields increases membrane permeability in glioblastoma cells," Proceedings of the 110th Annual Meeting of the American Association for Cancer Research, Mar. 29-Apr. 3, 2019, Atlanta, Georgia, Abstract nr250.

International Search Report and Written Opinion issued in application No. PCT/IB2019/057091 dated Dec. 17, 2019.

Kessler et al., "Effects of Tumor Treating Fields (TTFields) On Blood Brain Barrier (BBB) Permeability," Neuro. Onc., vol. 20, Suppl. 6, vi93-vi94, Nov. 2018.

Kessler et al., "Effects of Tumor Treating Fields (TTFields) on blood brain barrier permeability," Neuro. Onc., vol. 20, Suppl. 3, p. 286, Sep. 2018.

Kessler et al., "Effects of tumor treating fields (TTFields) on glioblastoma cells are augmented by mitotic checkpoint inhibition," Cell Death Discovery, 5:12, 2019.

Kessler et al., "Tumor treating fields (TTFields) affect the blood brain barrier (BBB) integrity in vitro and in vivo, Proceedings of the 110th Annual Meeting of the American Association for Cancer Research," Mar. 29-Apr. 3, 2019, Atlanta, Georgia, Abstract nr252.

Bonakdar et al., "Electroporation of Brain Endothelial Cells on Chip toward Permeabilizing the Blood-Brain Barrier," Biophysical Journal, vol. 110, pp. 503-513, Jan. 2016.

Hjouj et al., "MRI Study on Reversible and Irreversible Electroporation Induced Blood Brain Barrier Disruption," PLOS One, vol. 7, Issue 8, p. e42817, Aug. 2012.

Stupp et al., "Effect of Tumor-Treating Fields Plus Maintenance Temozolomide vs. Maintenance Temozolomide Alone on Survival in Patients with Glioblastoma: A Randomized Clinical Trial," JAMA, vol. 318, pp. 2306-2316, 2017.

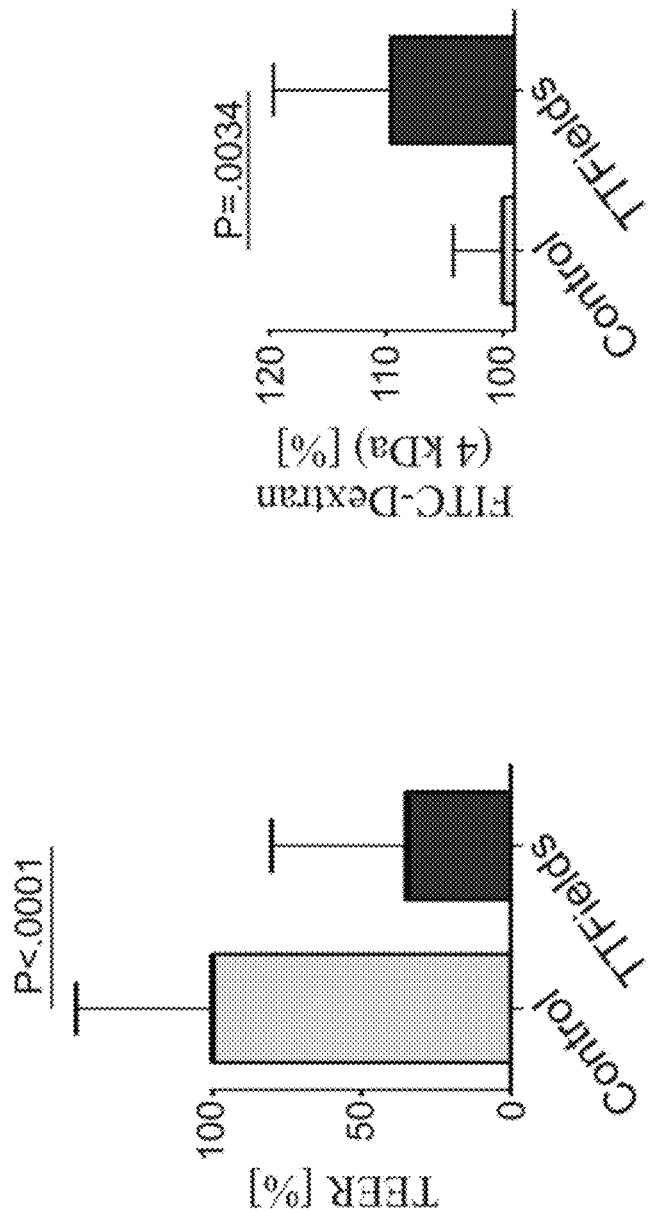

USING ALTERNATING ELECTRIC FIELDS TO INCREASE PERMEABILITY OF THE BLOOD BRAIN BARRIER

CROSS REFERENCE TO RELATED APPLICATIONS

This Application is a continuation of U.S. application Ser. No. 16/548,514, filed Aug. 22, 2019, which claims the benefit of U.S. Provisional Application 62/722,100, filed Aug. 23, 2018, each of which is incorporated herein by reference in its entirety.

BACKGROUND

Ordinarily, cerebral microvessels strictly regulate the transfer of substances between the blood and the brain tissue. This regulation by cerebral micro-vessels is called the blood-brain barrier (BBB), and is due to intercellular tight junctions (TJs) that form between brain capillary endothelial cells. In cerebral capillaries, TJs proteins are expressed 50-100 times more than in peripheral microvessels. TJs are formed by an intricate complex of transmembrane proteins (claudin and occludin) with cytoplasmic accessory proteins (ZO-1 and -2, cingulin, AF-6, and 7H6). By linking to the actin cytoskeleton, these proteins form a strong cell-cell connection. Brain endothelial cells, which form the endothelium of cerebral microvessels, are responsible for about 75-80% of the BBB's resistance to substances, and other cells such as astrocytes and pericytes provide the remainder of the resistance.

The BBB consists of tight junctions around the capillaries, and it ordinarily restricts diffusion of microscopic objects and large or hydrophilic molecules into the brain, while allowing for the diffusion of hydrophobic molecules (transcellular instead of paracellular transport).

In healthy people, the BBB serves a very important function because it prevents harmful substances (e.g. bacteria, viruses, and potentially harmful large or hydrophilic molecules) from entering the brain. There are, however, situations where the action of the BBB introduces difficulties. For example, it might be desirable to deliver large or hydrophilic drug molecules to treat a disease in the patient's brain. But when the BBB is operating normally, these drugs are blocked from entering the brain by the BBB.

SUMMARY OF THE INVENTION

One aspect of the invention is directed to a first method for delivering a substance across a blood brain barrier of a subject's brain. In this first method, the relevant substance can be delivered across a blood brain barrier of a subject's brain by applying an alternating electric field to the subject's brain for a period of time. Application of the alternating electric field to the subject's brain for the period of time increases permeability of the blood brain barrier in the subject's brain. The substance is administered to the subject after the period of time has elapsed, and the increased permeability of the blood brain barrier allows the substance to cross the blood brain barrier.

In some instances of the first method, the alternating electric field is applied at a frequency between 75 kHz and 125 kHz. In some instances of the first method, the period of time is at least 24 hours. In some instances of the first method, the period of time is at least 48 hours. In some instances of the first method, the alternating electric field has a field strength of at least 1 V/cm in at least a portion of the subject's brain. In some instances of the first method, the alternating electric field is applied at a frequency between 75 kHz and 125 kHz, the period of time is at least 24 hours, and the alternating electric field has a field strength of at least 1 V/cm in at least a portion of the subject's brain.

In some instances of the first method, the administering of the substance is performed intravenously. In some instances of the first method, the administering of the substance is performed orally. In some instances of the first method, the subject's brain is tumor-free.

In some instances of the first method, the substance comprises a drug for treating a disease. Examples of these instances include a cancer treatment drug, an infectious disease treatment drug, a neurodegenerative disease treatment drug, or an auto-immune disease treatment drug, an anti-epileptic drug, a hydrocephalus drug, a stroke intervention drug, or a psychiatric drug. In some instances of the first method, the substance is used for monitoring brain activity. Examples of these instances include a brain dye, a reporter, or a marker.

In any of the instances of the first method noted above, discontinuing the application of the alternating electric field may be done to allow the blood brain barrier to recover.

Another aspect of the invention is directed to a second method for delivering a substance across a blood brain barrier of a subject's brain. In this second method, the relevant substance can be delivered across a blood brain barrier of a subject's brain by applying an alternating electric field at a first frequency to the subject's brain for a period of time, wherein the first frequency is less than 190 kHz and the period of time is at least 24 hours, wherein application of the alternating electric field at the first frequency to the subject's brain for the period of time increases permeability of the blood brain barrier in the subject's brain. The substance is administered to the subject after the period of time has elapsed, and the increased permeability of the blood brain barrier allows the substance to cross the blood brain barrier.

In some instances of the second method, the alternating electric field is applied at a frequency between 75 kHz and 125 kHz. In some instances of the second method, the period of time is at least 48 hours. In some instances of the second method, the alternating electric field has a field strength of at least 1 V/cm in at least a portion of the subject's brain. In some instances of the second method, the alternating electric field is applied at a frequency between 75 kHz and 125 kHz, and the alternating electric field has a field strength of at least 1 V/cm in at least a portion of the subject's brain.

In any of the instances of the second method noted above, discontinuing the application of the alternating electric field may be done to allow the blood brain barrier to recover.

The methods described herein may be used to deliver a substance across the blood brain barrier of a subject's whose brain is tumor free. In this situation, another aspect of the invention is directed to a third method for delivering a substance across a blood brain barrier of a subject's brain. In this third method, the relevant substance can be delivered across a blood brain barrier of a subject's brain that does not include a tumor by applying an alternating electric field at a first frequency to the subject's brain for a period of time. The application of the alternating electric field at the first frequency to the subject's brain for the period of time increases permeability of the blood brain barrier in the subject's brain. The substance is administered to the subject after the period of time has elapsed, and the increased permeability of the blood brain barrier allows the substance to cross the blood brain barrier.

In some instances of the third method, the alternating electric field is applied at a frequency between 75 kHz and 125 kHz. In some instances of the third method, the period of time is at least 24 hours. In some instances of the third method, the period of time is at least 48 hours. In some instances of the third method, the alternating electric field has a field strength of at least 1 V/cm in at least a portion of the subject's brain. In some instances of the third method, the alternating electric field is applied at a frequency between 75 kHz and 125 kHz, the period of time is at least 24 hours, and the alternating electric field has a field strength of at least 1 V/cm in at least a portion of the subject's brain.

In any of the instances of the third method noted above, discontinuing the application of the alternating electric field may be done to allow the blood brain barrier to recover.

The methods described herein may be used to deliver a substance across the blood brain barrier of a subject with a brain tumor. In this situation, another aspect of the invention is directed to a fourth method for treating a tumor in a subject's brain and delivering a substance across a blood brain barrier of the subject's brain. In this fourth method, a first alternating electric field is applied at a first frequency to the subject's brain for a first period of time. Application of the first alternating electric field at the first frequency to the subject's brain for the first period of time increases permeability of the blood brain barrier in the subject's brain. The substance is administered to the subject after the first period of time has elapsed, and the increased permeability of the blood brain barrier allows the substance to cross the blood brain barrier. A second alternating electric field at a second frequency is applied to the subject's brain for a second period of time that is at least one week long. The second frequency is different from the first frequency, and the second alternating electric field at the second frequency has an intensity that is sufficiently large to inhibit the tumor.

In some instances of the fourth method, the first frequency is between 75 kHz and 125 kHz.

In some instances of the fourth method, the first frequency is between 50 kHz and 190 kHz. In some of these instances, the second frequency is between 190 kHz and 210 kHz.

In some instances of the fourth method, the first period of time is at least 24 hours. In some instances of the fourth method, the second period of time comprises a single uninterrupted interval of time that is at least one week long. In other instances of the fourth method, the second period of time comprises a plurality of non-contiguous intervals of time during which the second alternating electric field at the second frequency is applied to the subject's brain, wherein the plurality of non-contiguous intervals of time collectively add up to at least one week.

In any of the instances of the fourth method noted above, discontinuing the application of the alternating electric field may be done to allow the blood brain barrier to recover.

In some instances, any of the methods described above is used to deliver a substance having a molecular weight of at least 4 kDa across a blood brain barrier of a subject's brain.

In some instances, any of the methods described above is used to deliver a substance having a molecular weight of at least 69 kDa across a blood brain barrier of a subject's brain.

In some instances, any of the methods described above is used to deliver a substance across a blood brain barrier of a subject's brain, wherein the substance has at least one characteristic that ordinarily impedes the substance from crossing a non-leaky BBB.

Another aspect of the invention is directed to a first apparatus for treating a tumor in a subject's body and facilitating delivery of a substance across a blood brain barrier of the subject's body. The first apparatus comprises an AC voltage generator capable of operating at a first frequency between 50 and 190 kHz and a second frequency between 50 and 500 kHz. The second frequency is different from the first frequency. The AC voltage generator has a control input, and the AC voltage generator is configured to output the first frequency when the control input is in a first state and to output the second frequency when the control input is in a second state. The first apparatus also comprises a controller programmed to (a) place the control input in the second state so that the AC voltage generator outputs the second frequency, (b) accept a request to switch to the first frequency, (c) upon receipt of the request, place the control input in the first state so that the AC voltage generator outputs the first frequency for an interval of time, and (d) after the interval of time has elapsed, place the control input in the second state so that the AC voltage generator outputs the second frequency.

Some embodiments of the first apparatus further comprise a set of electrodes configured for affixation to the subject's body; and wiring that connects an output of the AC voltage generator to the set of electrodes.

In some embodiments of the first apparatus, the first frequency is between 75 kHz and 125 kHz, and the second frequency is between 150 kHz and 250 kHz. In some embodiments of the first apparatus, the interval of time is at least 24 hours. In some embodiments of the first apparatus, the interval of time is at least 72 hours. In some embodiments of the first apparatus, the controller is further programmed to, subsequent to the receipt of the request, switch the control input back and forth between the first state and the second state.

In some embodiments of the first apparatus, the AC voltage generator is capable of operating at at least one additional frequency between 50 and 500 kHz, and the AC voltage generator is configured to output the at least one additional frequency when the control input is in at least one additional state, and the controller is programmed to cycle the control input through the second state and the at least one additional state prior to receipt of the request, and to cycle the control input through the second state and the at least one additional state after the interval of time has elapsed.

Some embodiments of the first apparatus further comprise a user interface, and the request is accepted via the user interface. In some embodiments of the first apparatus, the request is accepted via radio frequency (RF).

BRIEF DESCRIPTION OF THE DRAWINGS

FIGS. 2A and 2B depict the results of integrity and permeability testing, respectively, on the artificial BBB.

DESCRIPTION OF THE PREFERRED EMBODIMENTS

This application describes a novel approach for temporarily increasing the permeability of the BBB using alternating electric fields so that substances that are ordinarily blocked by the BBB will be able to cross the BBB.

Figure 1:
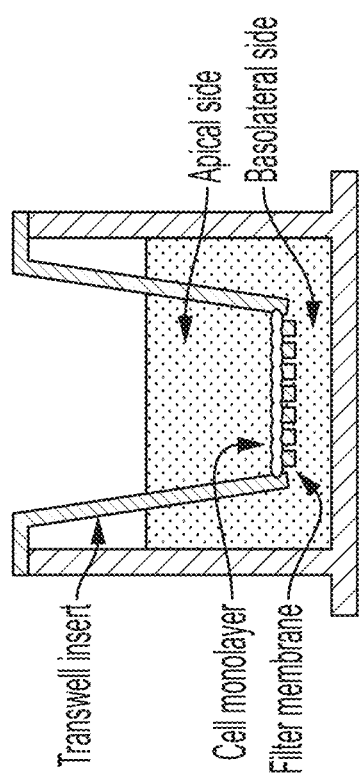
FIG. 1 depicts an exemplary setup for in vitro experiments in which imortilized murine brain capillary endothelial cells (cerebEND) were grown on coverslips and transwell inserts to create an artificial in vitro version of the BBB.

A set of in vitro experiments was run in which imortilized murine brain capillary endothelial cells (cerebEND) were grown on coverslips and transwell inserts to create an artificial in vitro version of the BBB, and FIG. 1 depicts the setup for these experiments. The cells were then treated with alternating electric fields (100-300 kHz) for 24 h, 48 h, and 72 h. The direction of the alternating electric fields was switched every 1 second between two perpendicular directions (i.e., 1 second in one direction followed by 1 second in the other direction, in a repeating sequence). The following effects were then analyzed: (a) Cell morphology (immuno-fluorescence staining of tight junction proteins Claudin 5 and ZO-1); (b) BBB integrity (using transendothelial electrical resistance (TEER)); and (c) BBB permeability (using fluoresceine isothiocyanate coupled to dextran (FITC) for flow cytometry).

A first set of experiments involved visualization of cell morphology and orientation, and visualization of the localization of stained proteins. This experiment was designed to ascertain how the frequency of the alternating electric field impacted the artificial BBB. Here, the cells were grown on coverslips, and alternating electric fields were applied for 72 hours at four different frequencies (100 kHz, 150 kHz, 200 kHz, and 300 kHz), with a field strength of 1.7 V/cm. The direction of the alternating electric fields was switched every 1 second between two perpendicular directions. There was also a control in which alternating electric fields were not applied. Cell morphology images depicting the presence of Claudin 5, ZO-1, and 4,6-diamidino-2-phenylindole (DAPI) in (each of which was stained a different color) were then obtained. Claudin 5 and ZO-1 indicate the presence of an intact BBB. This set of cell morphology images revealed that alternating electric fields disturb the artificial BBB by delocalization of tight junction proteins from the cell boundaries to the cytoplasm, with the most dramatic effects at 100 kHz.

A second set of experiments also involved visualization of cell morphology. This experiment was designed to ascertain how the duration of time during which the alternating electric field was applied impacted the artificial BBB. Endothelial cells were grown on coverslips, and an alternating electric field at a frequency of 100 kHz was applied for three different durations (24 h, 48 h, 72 h) plus a control. The direction of the alternating electric fields was switched every 1 second between two perpendicular directions. Cell morphology images depicting the presence of Claudin 5 and DAPI (each of which was stained a different color) were then obtained. This set of cell morphology images revealed that the phenomena discussed above in connection with the first set of experiments were already visible after 24 hours, and that the effects were most pronounced after 72 hours.

A third set of experiments also involved visualization of cell morphology. This experiment was similar to the second set of experiments, except that the endothelial cells were grown on transwell inserts instead of coverslips. The results were similar to the results of the second set of experiments. The delocalization of TJ proteins was visible after 24 hours and the effects were most pronounced after 72 hours. The three experiments described above support the conclusion that alternating electric fields cause structural changes in the cells, which might be responsible for an increase in BBB permeability.

FIGS. 2A and 2B depict the results of integrity and permeability testing, respectively, on the artificial BBB after subjecting it to alternating electric fields at a frequency of 100 kHz for 72 hours (with the direction of the alternating electric fields switched every 1 second between two perpendicular directions), and for a control. More specifically, FIG. 2A depicts the results of a transendothelial electrical resistance (TEER) test, which reveals that alternating electric fields reduced the integrity of the artificial BBB to 35% of the control. FIG. 2B depicts the results of a fluoresceine isothiocyanate (FITC) permeability test, which reveals that the alternating electric fields increased the permeability of the artificial BBB to FITC-dextrans with a 4 kDa molecular weight to 110% of the control. These experiments further support the conclusion that alternating electric fields increase the permeability of the BBB to molecules that ordinarily cannot traverse a non-leaky BBB.

Collectively, these in vitro experiments reveal that applying alternating electric fields at certain frequencies for a sufficient duration of time causes the delocalization of tight junction proteins (Claudin 5, ZO-1) from the cell boundaries to the cytoplasm (with the most dramatic effects at 100 kHz), and increases the permeability of the BBB. The alternating electric fields' effects appear already after 24 h and are most prominent after 72 h. More specifically, after using the alternating electric fields to increase the permeability of the BBB, molecules of 4 kDa can pass through the BBB.

Additional in vitro experiments were then conducted to determine what happens to the BBB after the alternating electric fields were turned off. These experiments used visualization of cell morphology to show how the artificial BBB recovers after discontinuing the alternating electric fields. In these experiments, endothelial cells were grown on coverslips and treated with 100 kHz alternating electric fields at a field strength of 1.7 V/cm for 72 hours. The direction of the alternating electric fields was switched every 1 second between two perpendicular directions. The alternating electric fields were then turned off, and the cells were followed for 96 hours after stopping the alternating electric field. Cell morphology images depicting the presence of Claudin 5 (stained) were obtained at 24 hours, 48 hours, 72 hours, and 96 hours. Those images revealed a progressive change in localization of Claudin between the cell boundaries and the cytoplasm on the 24 h, 48 h, 72 h, and 96 h images. Furthermore, a comparison of those four images to the respective images for the control (in which alternating electric fields were not applied during either the first 72 h or the last 96 h) revealed that the endothelial cell morphology was partially recovered 48 hours after stopping the alternating electric fields, and that the BBB was fully recovered (i.e., was comparable to the control) 96 hours after stopping the alternating electric fields.

Figures 3A, 3B:
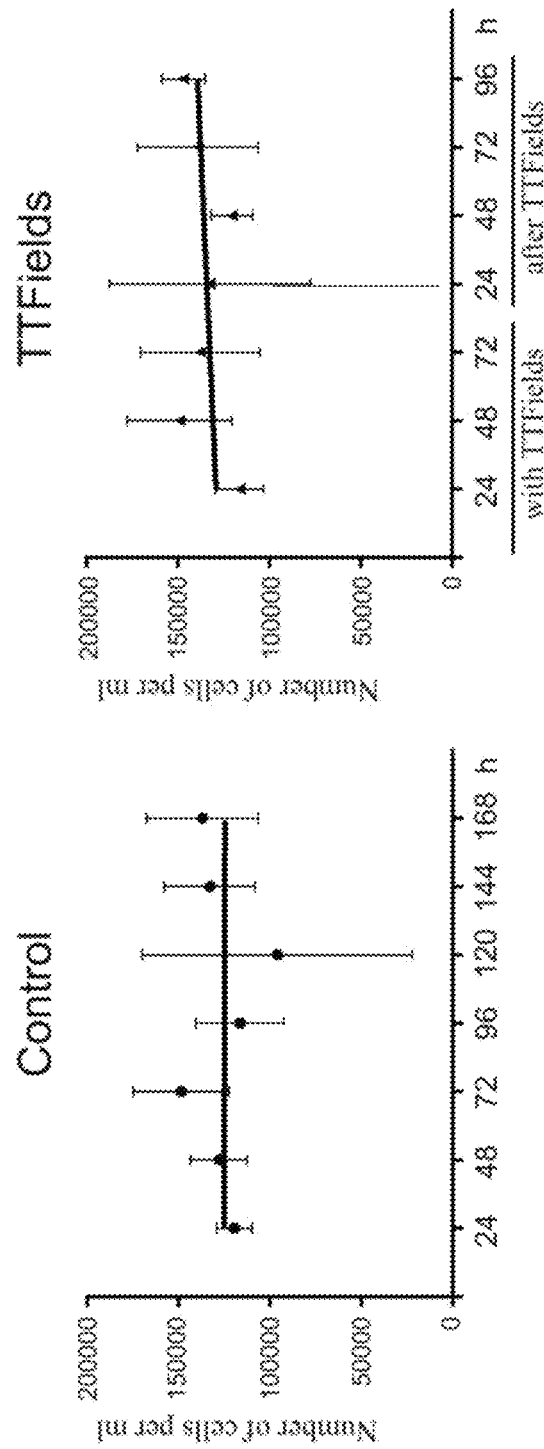
FIGS. 3A and 3B depict data showing that the increased permeability of the artificial BBB is not caused by cell death.

FIGS. 3A and 3B depict the results of an in vitro experiment designed to determine whether the observed changes in the permeability of the artificial BBB described above might be attributable to cell death. This experiment tested cell division by comparing cell counts (a) when alternating electric fields were applied for 72 hours followed by no alternating electric fields for 96 hours with (b) a control in which alternating electric fields were never applied. Endothelial cells were grown on coverslips and treated with 100 kHz alternating electric fields at a field strength of 1.7 V/cm for 72 hours. The direction of the alternating electric fields was switched every 1 second between two perpendicular directions. The alternating electric fields were then turned off, and the cells were followed for 96 hours after stopping the alternating electric field. The number of cells per ml for the alternating electric fields and the control were counted, and the results are depicted in FIGS. 3A and 3B (for control and for alternating electric fields, respectively). These results reveal that there was no statistically significant increase in the cell numbers during or after application of the alternating electric fields, which indicates that the changes in the BBB permeability noted above could not be attributed to cell death.

Another in vitro experiment used a TUNEL assay for apoptosis to determine whether the observed changes in the permeability of the artificial BBB described above might be attributable to cell death. In this experiment, endothelial cells were grown on coverslips and treated with 100 kHz alternating electric fields at a field strength of 1.7 V/cm for 72 hours. The direction of the alternating electric fields was switched every 1 second between two perpendicular directions. In the control, alternating electric fields were not applied. Cell morphology images depicting apoptosis (TUNEL) and Nuclei (DAPI) (each of which was stained a different color) were obtained after 24, 48, and 72 hours. None of those images revealed additional evidence of apoptosis, indicating that alternating electric fields did not cause cell death. This confirms that the changes in the BBB permeability noted above were not attributable to cell death.

A set of in vivo experiments on rats was also run to quantify the increase in vessel permeability caused by exposure to the alternating electric fields. These experiments used Evans Blue (EB) dye, which is an azo dye that has a very high affinity for serum albumin (molecule size ~69 kDa). Because of its large molecule size, serum albumin will ordinarily not be able to get past the BBB. But if the permeability of the BBB has been sufficiently increased, some of the serum albumin molecules (together with the EB dye that has been bound thereto) will make it across the BBB and can then be detected by looking for the EB in the rat's brain.

In this set of experiments, 100 kHz alternating electric fields were applied to the rat's brain for 72 hours, and the direction of the alternating electric fields was switched every 1 second between two perpendicular directions. This was accomplished by shaving each rat's head, positioning a first pair of capacitively coupled electrodes on the top and bottom of the rat's head, and positioning a second pair of capacitively coupled electrodes on the left and right sides of the rat's head. A 100 kHz AC voltage was then applied between the top and bottom electrodes for 1 second, followed by a 100 kHz AC voltage applied between the right and left electrodes for 1 second, in a repeating sequence.

Under the conditions indicated in Table 1 and for the times indicated on Table 1, EB was injected intravenously into the tail vein under anesthesia (Once injected, EB immediately binds to Albumin), and the EB was allowed to circulate for 2 hours in all cases. The following steps were then performed: (a) intracardiac perfusion with saline; (b) brains are sliced in four pieces with a brain slicer; (c) pieces were photographed to localize staining and weighted; (d) EB extraction after tissue homogenization with TCA 50% (1:3) and centrifuge and (e) EB quantification at 610 nm. Results are given as µg EB per g tissue.

TABLE 1

| Group # | Treatment | # of Rats | Time of EB Injection |
| --- | --- | --- | --- |
| 1 | 72 hours 100 kHz fields | 3 | 2 h before the end of the 72 h period |
| 2 | 72 hours 100 kHz fields + 2 hours rest | 3 | 2 h after the end of the 72 h period |
| 3 | 72 hours heat using sham electrodes | 3 | 2 h before the end of heat |
| 4 | Control (no fields + no heat) | 3 | Same time as group 1 |

During the experiment, two animals from group 2 and one animal from group 4 were excluded (disrupted treatment, failure to inject EB into the tail vein). There were no differences between the animals treated with alternating electric fields (groups 1 and 2) and therefore these animals were grouped together. Similarly, there were no differences between sham heat and control animals (groups 3 and 4) and therefore these animals were grouped together.

Figure 4:
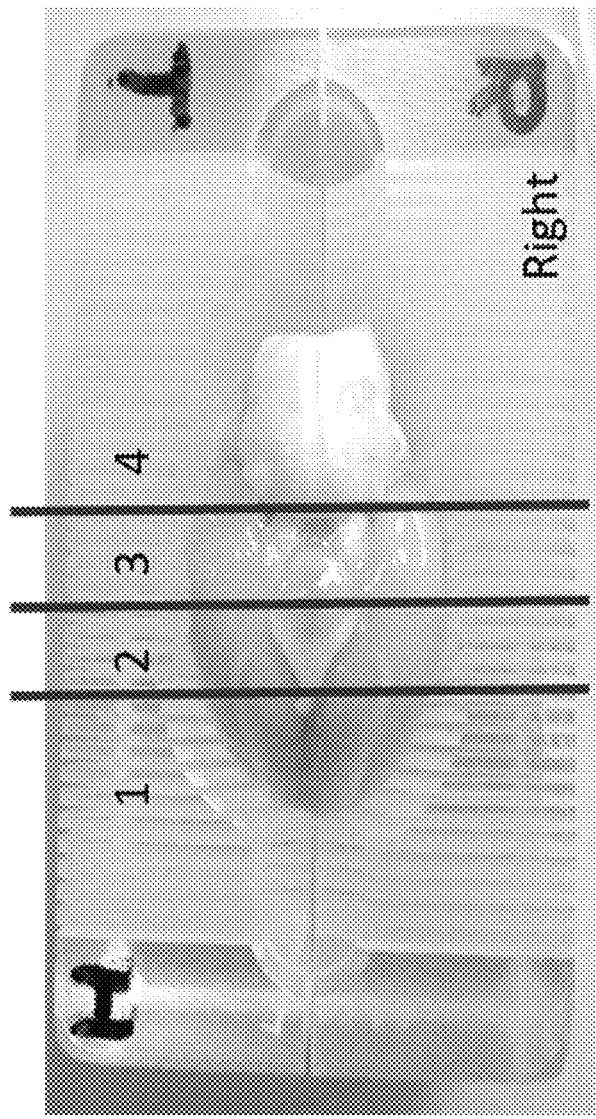
FIG. 4 depicts the positions at which rats' brains were sliced for an in vivo experiment.

The rats' brains were sliced into four pieces using a brain slicer at the positions shown in FIG. 4. EB accumulation in these four specific sections was then measured. In addition, a computer simulation was performed to determine the field strength in each of these four sections. Table 2 specifies the field strength obtained from the simulation in each of these four sections, with all values given in V/cm RMS.

TABLE 2

| | Section | | | |
| --- | --- | --- | --- | --- |
| | 1 | 2 | 3 | 4 |
| Mean Field Strength | 2.7 V/cm | 3 V/cm | 2.6 V/cm | 1.6 V/cm |
| Media Field Strength | 2.5 V/cm | 2.6 V/cm | 2.4 V/cm | 1.6 V/cm |

Figure 5:
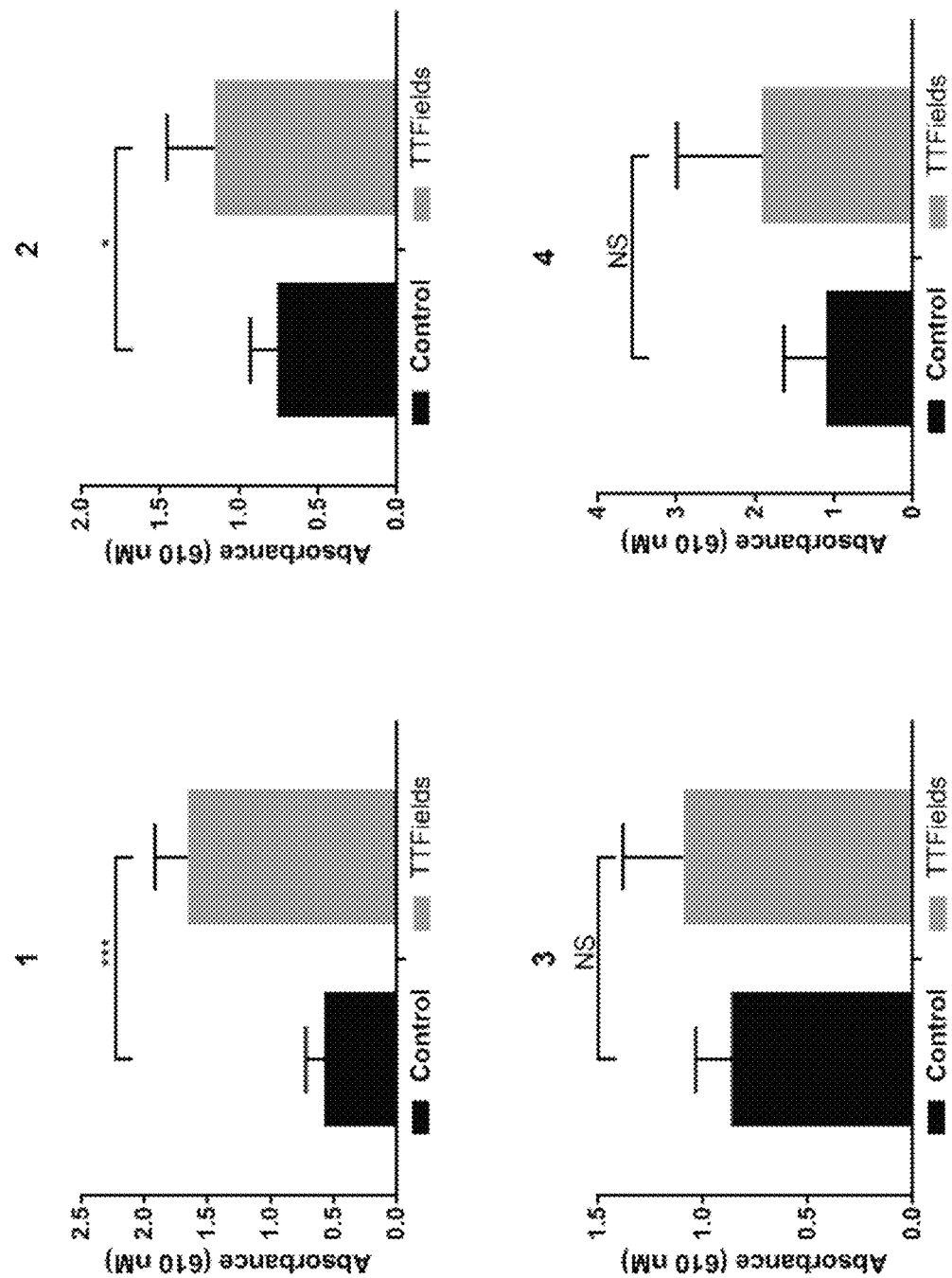
FIG. 5 depicts the EB accumulation for this in vivo experiment in different sections of the rats' brains.

The results for EB accumulation in sections 1 through 4 are depicted in FIG. 5. The summary of these results is as follows: (1) a statistically significant increase was observed in sections 1, 2 (frontal cerebrum) where the field strength was highest; and a smaller increase (that was not statistically significant) was observed in the more posterior sections (3, 4) where the field strength was lower.

Figure 6:
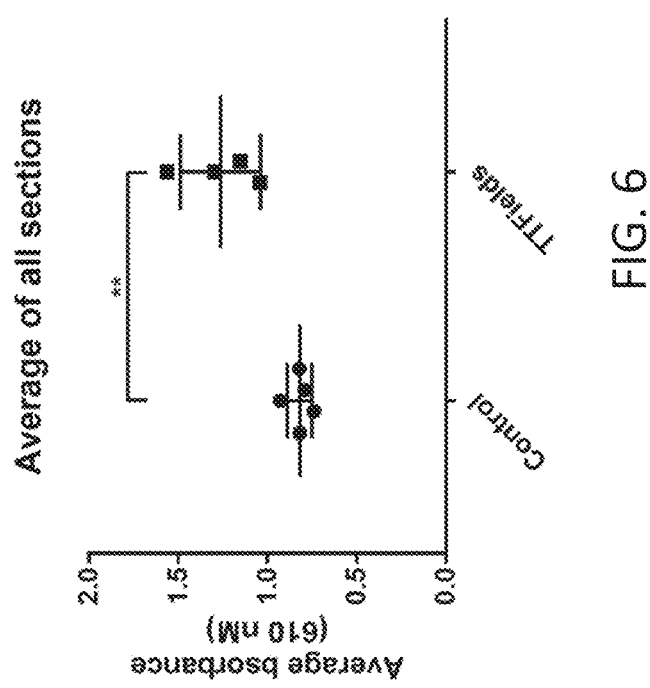
FIG. 6 depicts the average EB accumulation in the rat brain for this in vivo experiment, averaged over all sections.

FIG. 6 depicts the average EB accumulation in the rat brain, averaged over all four sections 1-4. This result reveals higher accumulation of EB in the brains of rats treated with alternating electric fields for 72 hours, and this result was statistically significant ($p<0.05$).

The in vivo experiments described above establish that: (1) alternating electric fields application permits the BBB passage of molecules of average molecular size of ~69 kDa to the brain tissue; (2) the increase in permeability of the BBB is maintained 2 hours after terminating the alternating electric fields application; and (3) the increased permeability of the BBB varies between different sections of the brain. The latter may be the result of the different field strengths that were imposed in the various sections of the brain. These experiments further support our conclusion that alternating electric fields increase the permeability of the BBB to molecules that ordinarily cannot traverse a non-leaky BBB.

In another set of in vivo experiments, 5 rats were treated with alternating electric fields at 100 kHz for 72 h, and 4 control rats were not treated with alternating electric fields for the same period of time. At the end of the 72 hour period, the fluorescent compound TRITC-Dextran of 4 kDa was injected intravenously into the tail vein under anesthesia, and allowed to circulate for 2 minutes in all cases. The brains were then removed, frozen, sectioned and scanned with a fluorescent scanner. All slides were scanned with the same conditions. The resulting images revealed significantly higher levels of accumulation of the fluorescent 4 kDA TRITC-Dextran in the brain tissue of the rats that were subjected to alternating electric fields (as compared to the control), confirming yet again that alternating electric fields increase the permeability of the BBB.

Yet another set of in vivo experiments was performed using Dynamic Contrast Enhanced MRI (DCE-MRI) with intravenous injection of Gadolinium contrast agent (Gd-DTPA, Magnetol, MW 547). In these experiments, test rats were treated with 100 kHz alternating electric fields for 72 h, and control rats were not treated with alternating electric fields for the same period of time. After this 72 h period, the alternating electric field was turned off, the rats were anesthetized, and a series of 60 T1w MRI scans (each of the scans having a duration of 28 seconds) was acquired. The gadolinium contrast agent was injected into the rat's tail vein during the 7th of these 60 scans.

The image analysis for each rat included (1) determining a baseline for each voxel by calculating the mean of the first six T1w MRI scans for each voxel (i.e., the scans prior to the injection of the gadolinium); (2) computing voxel by voxel, the percent signal change (i.e., gadolinium accumulation) over time relative to the baseline; (3) segmenting the brain into anterior, middle, and posterior segments; (4) generating for each of the three segments the mean percent signal change with respect to the baseline over all the voxels in the respective segment and then (5) averaging 4 consecutive time points (i.e. 4 scans) together. Finally, the data from all of the rats within any given group were averaged together.

Figure 7:
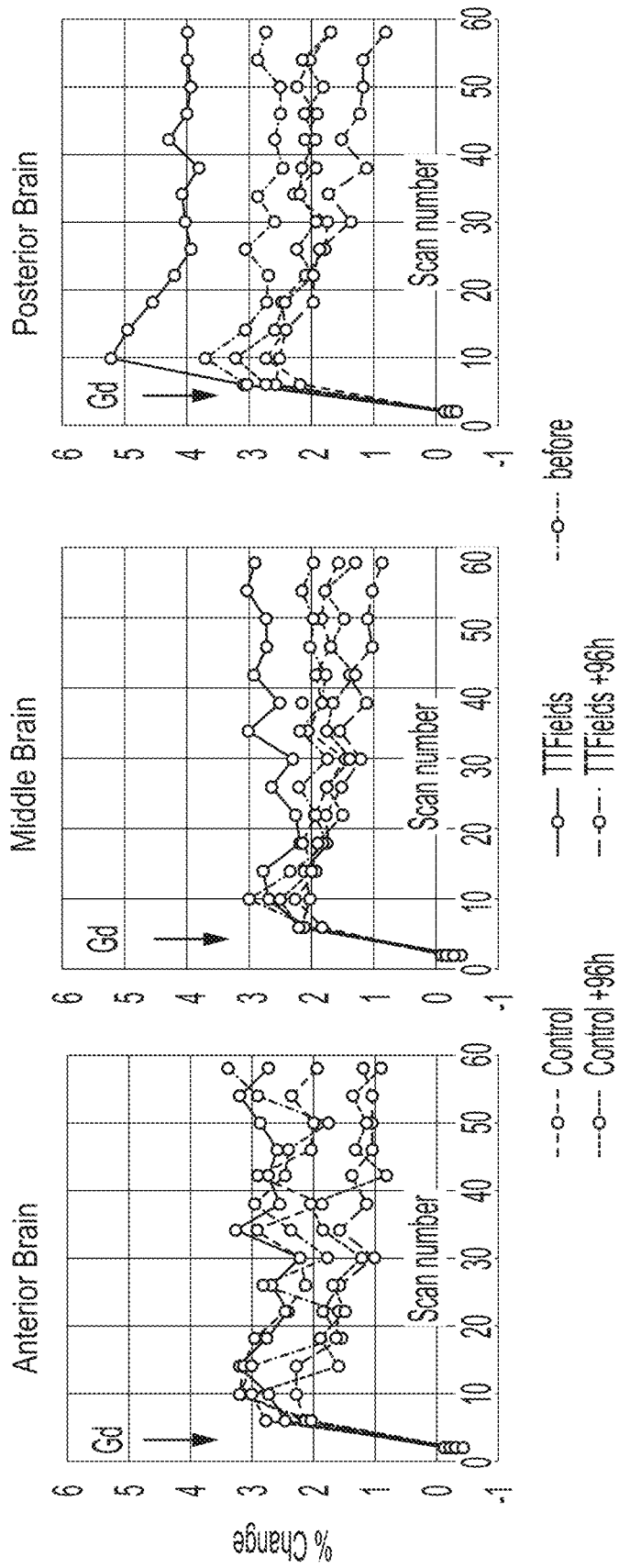
FIG. 7 depicts the increase in BBB permeability in three different sections of rat brains that is induced by alternating electric fields in vivo, as determined using contrast enhancement MRIs.

The results of this DCE-MRI experiment for each of the three segments of the brain (i.e. anterior, middle, and posterior) are depicted in FIG. 7. This data reveals that contrast agent accumulation in the brain tissue of rats that were treated with alternating electric fields (trace labeled TTFields; n=6) was significantly higher than in the control rats (trace labeled control; n=3). Moreover, the distinction was most pronounced in the posterior brain, which is the portion of the brain where the alternating electric fields had the highest field strength. From this we can conclude that the alternating electric fields successfully increased the permeability of the BBB in vivo.

Figure 8:
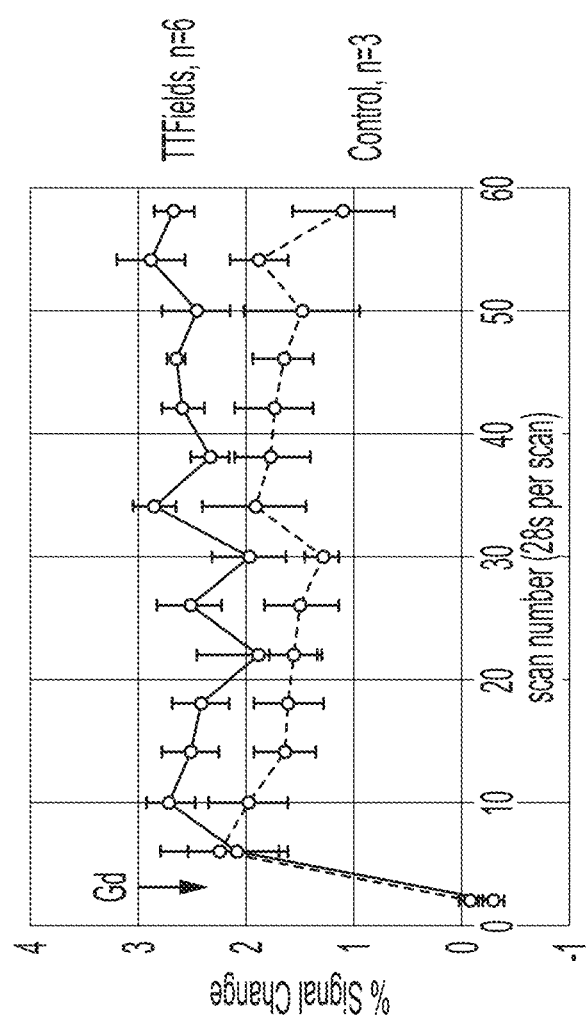
FIG. 8 depicts the increase in BBB permeability in rat cortexes that is induced by alternating electric fields in vivo, as determined using contrast enhancement MRIs.

To test whether this increase in permeability of the BBB was temporary, the same test conditions were repeated, but followed with an additional 96 hours without alternating electric fields. After this 96 hour period, a series of 60 T1w MRI scans (each of the scans having a duration of 28 seconds) was acquired using the same procedure described above (including the gadolinium injection). The results of this portion of the DCE-MRI experiment for each of the three segments of the brain are also depicted in FIG. 8. This data reveals that contrast agent accumulation in the brain tissue of rats that were treated with alternating electric fields for 72 hours followed by 96 hours without alternating electric fields (trace labeled TTFields+96h; n=7) was not significantly different from the control rats (trace labeled control+96h; n=3). From this we can conclude that the permeability of the BBB returns to normal after the alternating electric fields are discontinued.

An additional series of 60 T1w MRI scans (each of the scans having a duration of 28 seconds) was also acquired using the same procedure before the alternating electric field was applied to the rats (n=2). The results of this portion of the DCE-MRI experiment for each of the three segments of the brain (i.e. anterior, middle, and posterior) are also depicted in FIG. 8 (see the trace labeled "before").

FIG. 8 shows the average of all 3 segments of the brain (i.e. anterior, middle, and posterior) for 72 h of TTFields (n=6) and a control of no TTFields for 72 h (n=3), with standard deviation bars. A paired t test was used to compare between the two groups, and $p<0.0001$.

We note that the upper size limit of molecules that can pass through the BBB after applying the alternating electric fields has not yet been determined. But based on (a) the in vitro experiments described herein using FITC-dextrans with a 4 kDa molecular weight and (b) the in vivo experiments described herein using EB (which binds to serum albumin having a molecule size of ~69 kDa), the upper limit appears to be at least about 69 kDa, and is most certainly at least 4 kDa.

The implications of being able to reversibly increase the permeability of the BBB at will are far-reaching, because it now becomes possible to deliver many substances across the BBB of a subject, despite the fact that those substances have at least one characteristic that ordinarily impedes the substance from crossing a non-leaky BBB. Many of these implications involve delivering a substance including but not limited to treating agents and diagnostic agents across a blood brain barrier of a subject's brain.

Examples include but are not limited to the following: delivering chemotherapeutic agents across the BBB to treat cancer (in this context, it may be possible to lower the dosage of drugs for the treatment of brain tumors and metastases with severe side effects in other parts of the body based on the increased permeability of the drugs to the brain); delivering antibodies and/or cell-based therapies across the BBB for immunotherapy; delivering contrast agents dyes, reporters, and markers across the BBB for diagnostic purposes and for research (e.g. monitoring brain activity); delivering antibacterial agents across the BBB to treat infectious diseases; delivering anti-viral agents or virus neutralizing antibodies across the BBB to treat viral infections; delivering anti-parasitic agents across the BBB to treat parasites; delivering agents to treat neurodegenerative and autoimmune disease across the BBB; delivering psychiatric drugs; delivering anti-epileptic drugs; delivering hydrocephalus drugs; delivering stroke intervention and recovery drugs; delivering compounds that are lacking in the brain across the BBB to treat conditions in which those compounds are lacking (e.g., for treating Parkinson's disease, etc.).

While the testing described above was done in vitro and in live rats, it is expected that similar results will be obtained with other animals and with humans.

The methods described herein can also be applied in the in vivo context by applying the alternating electric fields to a live subject's brain. Imposing the electric field in the subject's brain will increase the permeability of the BBB, which will enable molecules that are ordinarily blocked or impeded by the BBB to get through. This may be accomplished, for example, by positioning electrodes on or below the subject's skin so that application of an AC voltage between selected subsets of those electrodes will impose the alternating electric fields in the subject's brain.

For example, one pair of electrodes could be positioned on the front and back of the subject's head, and a second pair of electrodes could be positioned on the right and left sides of the subject's head. In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body. In another embodiment, electrodes could be inserted subcutaneously below a patient's skin.

An AC voltage generator applies an AC voltage at a selected frequency (e.g., 100 kHz, or between 50 and 190 kHz) between the right and left electrodes for a first period of time (e.g. 1 second), which induces alternating electric fields where the most significant components of the field lines are parallel to the transverse axis of the subject's head. Then, the AC voltage generator applies an AC voltage at the same frequency (or a different frequency) between the front and back electrodes for a second period of time (e.g. 1 second), which induces alternating electric fields where the most significant components of the field lines are parallel to the sagittal axis of the subject's head. This two step sequence is then repeated for the duration of the treatment. Optionally, thermal sensors may be included at the electrodes, and the AC voltage generator can be configured to decrease the amplitude of the AC voltages that are applied to the electrodes if the sensed temperature at the electrodes gets too high. In some embodiments, one or more additional pairs of electrodes may be added and included in the sequence. In alternative embodiments, only a single pair of electrodes is used, in which case the direction of the field lines is not switched. Note that any of the parameters for this in vivo embodiment (e.g., frequency, field strength, duration, direction-switching rate, and the placement of the electrodes) may be varied as described above in connection with the in the vitro embodiments. But care must be taken in the in vivo context to ensure that the electric field remains safe for the subject at all times.

A wide variety of applications for increasing the permeability of the BBB can be readily envisioned in the in vivo context. In one example, localized enhancement of drug uptake by tumor cells (e.g., glioblastoma cells) in the brain can be induced by applying alternating electric fields to the brain for a period of time (e.g., 72 hours or at least 24 hours) prior to and during administration of chemotherapies or other antineoplastic agents.

Figure 9:
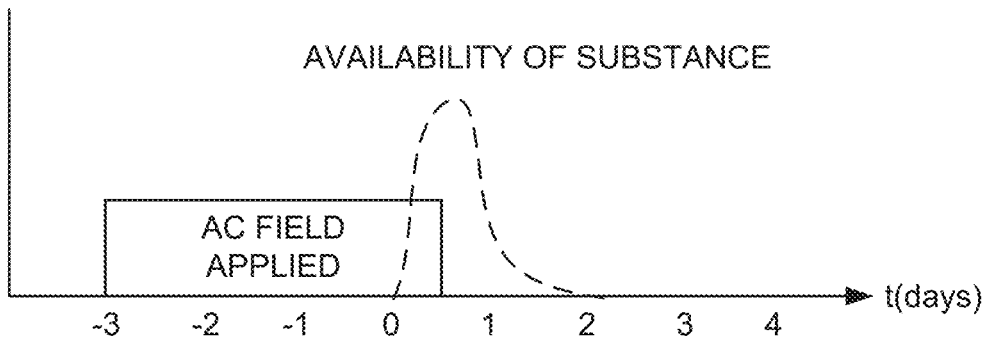
FIG. 9 depicts a suitable timing relationship between the application of the alternating electric field and the administration of the substance to the subject.

FIG. 9 depicts a suitable relationship in timing between the application of the alternating electric field and the administration of the substance to a live patient. Based on the data described above, and assuming that the substance is introduced or administered at a given time t=0, the alternating electric field can begin before the given time (e.g., 72 hours before t=0), and continue for an interval of time after the given time (e.g., until 12 hours following t=0). In this situation, the permeability of the BBB will begin to increase before the substance is administered and before the substance reaches the BBB. This will enable the substance to cross the BBB immediately upon its arrival. In the context of chemotherapy, this would correspond to starting application of the alternating electric fields, administering the chemotherapeutic agent 72 hours later, followed by application of the alternating electric fields for an additional interval of time (e.g., until 12 hours following the time at which the chemotherapeutic agent was administered).

Note that the intervals of time discussed above in connection with FIG. 9 can either be uninterrupted or can include breaks that are preferably short. For example, a 12 hour interval could be satisfied by a single uninterrupted block of 12 hours. Alternatively, the 12 hour interval could be satisfied by applying the alternating electric fields for 6 hours, followed by a 1 hour break, followed by applying the alternating electric fields for an additional 6 hours. Similar breaks may also optionally interrupt the 72 hour interval that precedes the administration of the substance. Note also that in the context of FIG. 9, when the substance is administered to a live patient, the administration of the substance may be performed using any of a variety of approaches including but not limited to intravenously, orally, subcutaneously, intrathecal, intraventricularly, and intraperitonealy.

In some preferred embodiments, the frequency of the alternating electric fields is less than 190 kHz (e.g., between 50 and 190 kHz or between 25 and 190 kHz). Based on the experiments discussed above, using a frequency of less than 190 kHz combined with a period of time of at least 24 hours will increase the change in permeability (as compared to operating outside of those ranges).

The methods described herein may be used to deliver a substance across the blood brain barrier of a subject's brain when the subject's brain includes a tumor. One existing approach to treating brain tumors (e.g., glioblastoma) is by applying alternating electric fields at frequencies between 50 and 500 kHz, preferably between 100 and 300 kHz to the tumor. For glioblastoma, 200 kHz is the most preferred frequency. Alternating electric fields at these frequencies are referred to as TTFields, and are described in U.S. Pat. Nos. 6,868,289 and 7,565,205, each of which is incorporated herein by reference in its entirety. Briefly, those two applications describe disrupting dividing cells during mitosis. The effectiveness of TTFields is improved when the direction of the electric field is periodically switched, when the strength of the field in at least a portion of the tumor is at least 1 V/cm, and when the fields are applied for long periods of time (e.g., weeks or months) with as few breaks as possible.

In patients with brain tumors, situations may arise where it will be desirable to treat the tumor with TTFields and also deliver a substance across the same patient's blood brain barrier (e.g., to help get a therapeutically effective amount of a chemotherapy drug past the BBB to provide an additional line of attack against the tumor). In some situations, it may be possible to use a single frequency of an alternating electric field to both treat the tumor and increase the permeability of the BBB. In other situations, it may be desirable to use alternating electric fields with different frequencies: a first frequency that is selected to provide improved results for increasing the permeability of the BBB, and a second frequency that is selected to provide improved results for the anti-tumor action of the TTFields.

Figure 10:
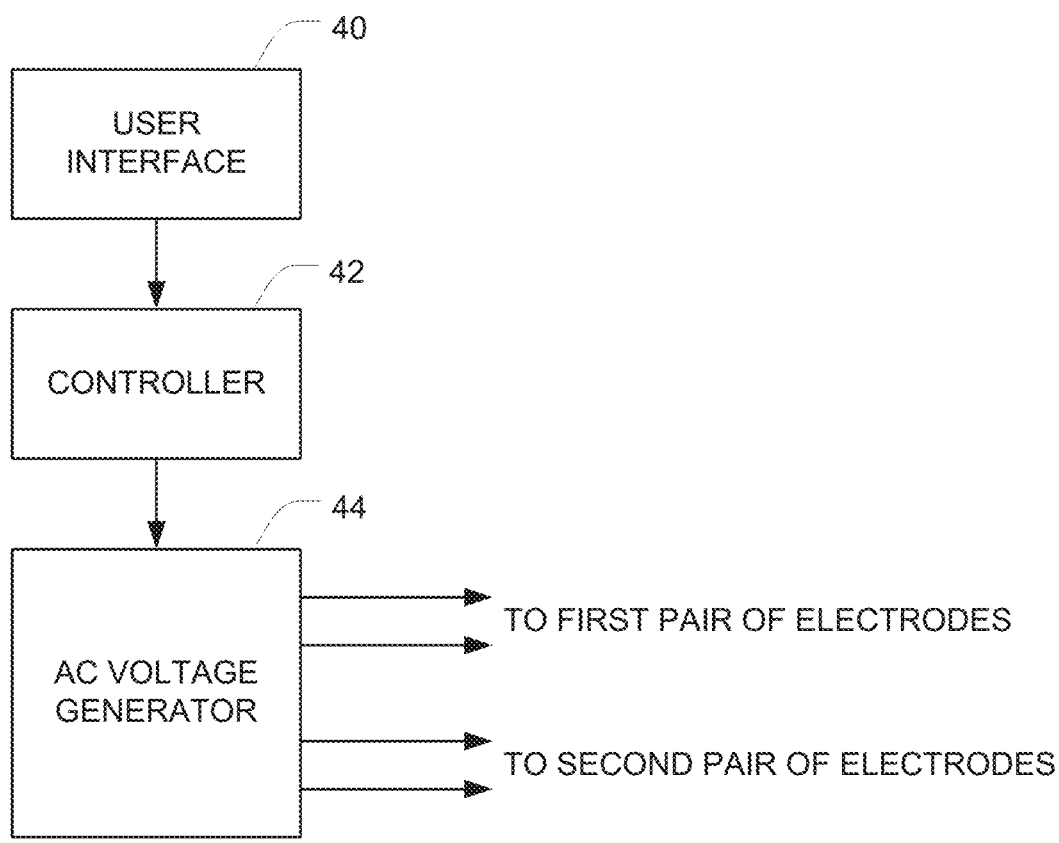
FIG. 10 is a block diagram of a dual-frequency apparatus that generates a first frequency for inducing BBB permeability and a second frequency for inducing cytotoxicity.

FIG. 10 is a block diagram of an apparatus that generates a first frequency for inducing BBB permeability and a second frequency for inducing cytotoxicity. The apparatus includes an AC voltage generator 44 that is similar to the conventional Optune® field generator unit, but has the ability to operate at two different frequencies. The first frequency is between 50 and 190 kHz and the second frequency is between 50 and 500 kHz. In some embodiments, the first frequency is between 75 kHz and 125 kHz and the second frequency is between 150 kHz and 250 kHz.

The ability to operate at two different frequencies may be implemented, for example, using relays to switch either a first set of components or a second set of components into the conventional circuit that generates the AC voltage, and adjusting the operating frequency of an oscillator. The AC voltage generator 44 is configured to output either the first frequency or the second frequency depending on the state of a control input. When the control input is in a first state the AC voltage generator 44 outputs the first frequency, and when the control input is in a second state the AC voltage generator 44 outputs the second frequency. A controller 42 is programmed to place the control input in the second state so that the AC voltage generator 44 outputs the second frequency. The controller 42 is also programmed to accept a request to switch to the first frequency. In the embodiment depicted in FIG. 10, the request arrives via a user interface 40 that may be implemented using any of a variety of conventional approaches including but not limited to a pushbutton, a touch screen, etc. In alternative embodiments, the request may arrive via RF (e.g. Bluetooth, WiFi, etc.) from a tablet, smartphone, etc.

Upon receipt of the request, the controller 42 will place the control input in the first state so that the AC voltage generator 44 will output the first frequency for an interval of time (e.g., 72 hours). After the interval of time has elapsed, the controller 42 will place the control input in the second state so that the AC voltage generator 44 reverts to outputting the second frequency.

Optionally, the AC voltage generator 44 may be configured to output one or more additional frequencies (e.g., a third frequency, a fourth frequency, etc.), depending on the state of the control input. Preferably each of these additional frequencies is selected to induce cytotoxicity. In these embodiments, the controller 42 is programmed to cycle the control input through the states that cause the AC voltage generator 44 to output the second frequency and the one or more additional frequencies before the request arrives. The controller 42 is also programmed to accept a request to switch to the first frequency. Upon receipt of the request, the controller 42 will place the control input in the first state so that the AC voltage generator 44 will output the first frequency for an interval of time (e.g., 72 hours). After the interval of time has elapsed, the controller 42 will revert to cycling the control input through the states that cause the AC voltage generator 44 to output the second frequency and the one or more additional frequencies.

The system depicted in FIG. 10 is particularly useful when a person has a tumor that is being treated by combination therapy that includes TTFields and chemotherapy. In this situation, the system operates most of the time at the second frequency to provide the maximum cytotoxicity effect. But before a person visits a chemotherapy clinic for a dose of chemotherapy, healthcare personnel (or the user) actuates the user interface 40 to switch the system to the first frequency that promotes BBB permeability. In this situation, the actuation of the user interface could be done e.g., 72 hours before the expected start of the chemotherapy.

Alternatively, upon receipt of the request (e.g., from the user interface 40), the controller 42 can control the control input so that the AC voltage generator 44 will output the first frequency for an interval of time (e.g., 1 hour), then switch back and forth between the second frequency and the first frequency (e.g., switching every hour). Eventually (e.g., when the relevant substance has been exhausted from the patient's bloodstream), the controller 42 controls the control input so that the AC voltage generator 44 reverts to outputting the second frequency.

A set of electrodes (not shown) that are similar to the conventional electrodes used with Optune® are connected to the output of the AC voltage generator 44.

Note that in connection with any of the methods described above, the BBB should recover to its original low-permeability state after a sufficient amount of time has elapsed following the termination of the alternating electric field. This can be important in many contexts for the safety of the subject.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method for delivering a substance across a blood brain barrier of a subject's brain, the method comprising:
   applying an alternating electric field at a first frequency to the subject's brain for a period of time, wherein the subject's brain is tumor-free, wherein the first frequency is between 50 kHz and 190 kHz, and wherein application of the alternating electric field at the first frequency to the subject's brain for the period of time increases permeability of the blood brain barrier in the subject's brain; and
   administering the substance to the subject, wherein the increased permeability of the blood brain barrier allows the substance to cross the blood brain barrier,
   wherein the period of time is at least 24 hours and the substance is administered to the subject after the period of time has elapsed.

2. The method of claim 1, wherein the alternating electric field is applied at a frequency between 75 kHz and 125 kHz,
   wherein the alternating electric field has a field strength of at least 1 V/cm in at least a portion of the subject's brain.

3. A method of delivering a substance across a biological barrier in a subject's body, the method comprising:
   applying an alternating electric field to the biological barrier in a portion of the subject's body for a period of time, wherein the alternating electric field has a frequency between 50 kHz and 190 kHz, and wherein application of the alternating electric field for the period of time increases permeability of the biological barrier; and
   administering the substance to the subject, wherein the increased permeability of the biological barrier allows the substance to cross the biological barrier,
   wherein the portion of the subject's body is tumor-free,
   wherein the period of time is at least 24 hours and the substance is administered to the subject after the period of time has elapsed, and
   wherein the alternating electric field has a field strength of at least 1 V/cm in at least a part of the portion of the subject's body.

4. A method of delivering a substance across a biological barrier in a subject's body, wherein the biological barrier includes endothelial cells and tight junction proteins located between the endothelial cells, the method comprising:
   applying an alternating electric field to the endothelial cells in a portion of the subject's body for a period of time, wherein the alternating electric field has a frequency between 50 kHz and 190 kHz, and wherein application of the alternating electric field for the period of time causes delocalization of the tight junction proteins; and administering the substance to the subject, wherein the delocalization of the tight junction proteins allows the substance to cross the biological barrier, wherein the portion of the subject's body is tumor-free, and wherein the substance is administered after the period of time has elapsed.

5. The method of claim 4, wherein the alternating electric field has a field strength of at least 1 V/cm in at least a part of the portion of the subject's body.

6. The method of claim 4, wherein the period of time is at least 24 hours, and the alternating electric field has a field strength of at least 1 V/cm in at least a part of the portion of the subject's body.

7. The method of claim 4, wherein the tight junction proteins include claudin.

8. The method of claim 4, wherein the tight junction proteins include claudin-5.

9. The method of claim 4, wherein the tight junction proteins include ZO-1.

10. The method of claim 4, wherein the substance is administered at least 24 hours after the applying of the alternating electric field has begun.

11. The method of claim 4, wherein the substance is administered within 96 hours of when the period of time elapsed.

12. The method of claim 4, wherein the substance has a molecular weight between 4 kDa and 69 kDa.

* * * * *